US010470727B2

United States Patent
Ota et al.

(10) Patent No.: US 10,470,727 B2
(45) Date of Patent: Nov. 12, 2019

(54) X-RAY IMAGE CAPTURING APPARATUS

(71) Applicant: Konica Minolta, Inc., Chiyoda-ku, Tokyo (JP)

(72) Inventors: Ikuma Ota, Tokyo (JP); Ryouhei Kikuchi, Hachioji (JP); Yoshihiko Eguchi, Tokorozawa (JP)

(73) Assignee: KONICA MINOLTA, INC., Tokyo (JP)

( * ) Notice: Subject to any disclaimer, the term of this patent is extended or adjusted under 35 U.S.C. 154(b) by 260 days.

(21) Appl. No.: 15/586,822

(22) Filed: May 4, 2017

(65) Prior Publication Data
US 2017/0325762 A1    Nov. 16, 2017

(30) Foreign Application Priority Data

May 16, 2016    (JP) .................................. 2016-097542

(51) Int. Cl.
| | | |
|---|---|---|
| *A61B 6/00* | (2006.01) | |
| *G01T 7/00* | (2006.01) | |
| *H04N 5/32* | (2006.01) | |
| *H04N 5/374* | (2011.01) | |
| *H04N 5/378* | (2011.01) | |

(52) U.S. Cl.
CPC .............. *A61B 6/4283* (2013.01); *A61B 6/54* (2013.01); *G01T 7/00* (2013.01); *H04N 5/32* (2013.01); *H04N 5/374* (2013.01); *H04N 5/378* (2013.01); *A61B 6/4233* (2013.01)

(58) Field of Classification Search
CPC ....... A61B 6/4233; A61B 6/4283; A61B 6/54; G01T 7/00; H04N 5/32; H04N 5/374; H04N 5/378
See application file for complete search history.

(56) References Cited

U.S. PATENT DOCUMENTS

2014/0016749 A1*    1/2014    Oda ..................... A61B 6/5258
378/62

FOREIGN PATENT DOCUMENTS

| JP | 2014049982 A | 3/2014 |
|---|---|---|
| JP | 2015062012 A | 4/2015 |

OTHER PUBLICATIONS

Translation of JP 2015-062012 (Year: 2015).*

\* cited by examiner

*Primary Examiner* — Chih-Cheng Kao
(74) *Attorney, Agent, or Firm* — Cantor Colburn LLP

(57) ABSTRACT

An X-ray image capturing apparatus includes: scanning and signal lines; an X-ray sensor; detecting elements; a switching element to make charges accumulated in response to an OFF voltage and released in response to an ON voltage; a scan driving unit to switch a voltage applied to the scanning lines between ON and OFF voltages; a readout circuit to read the charges as image data; and a control circuit to detect an irradiation start by a first scheme based on a current increase due to X-ray irradiation or a second scheme based on an output from the X-ray sensor and to turn off the switching element to make charges accumulated if the first or second scheme detects the irradiation start, wherein a detection threshold is set such that the second scheme has a slower response and can detect an X-ray at a lower dose rate than the first scheme.

8 Claims, 9 Drawing Sheets

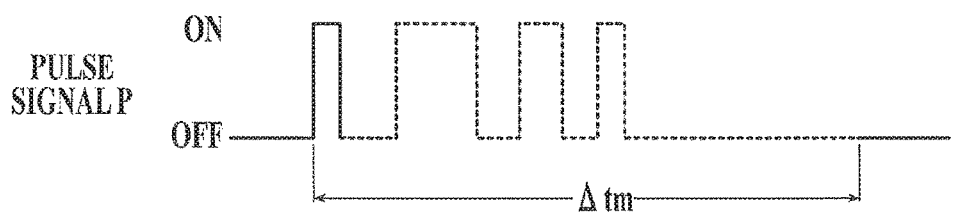
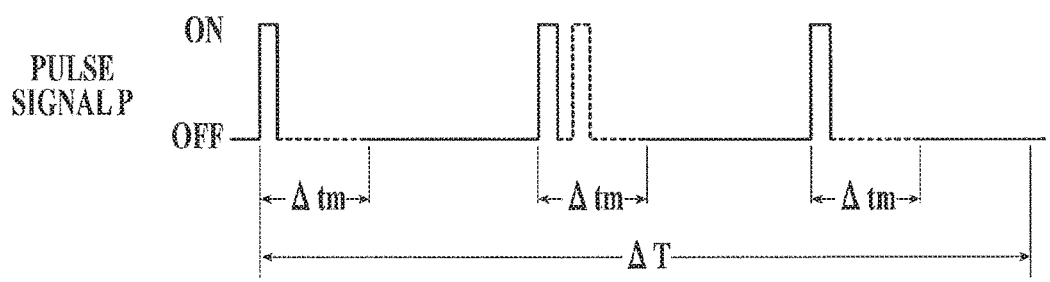
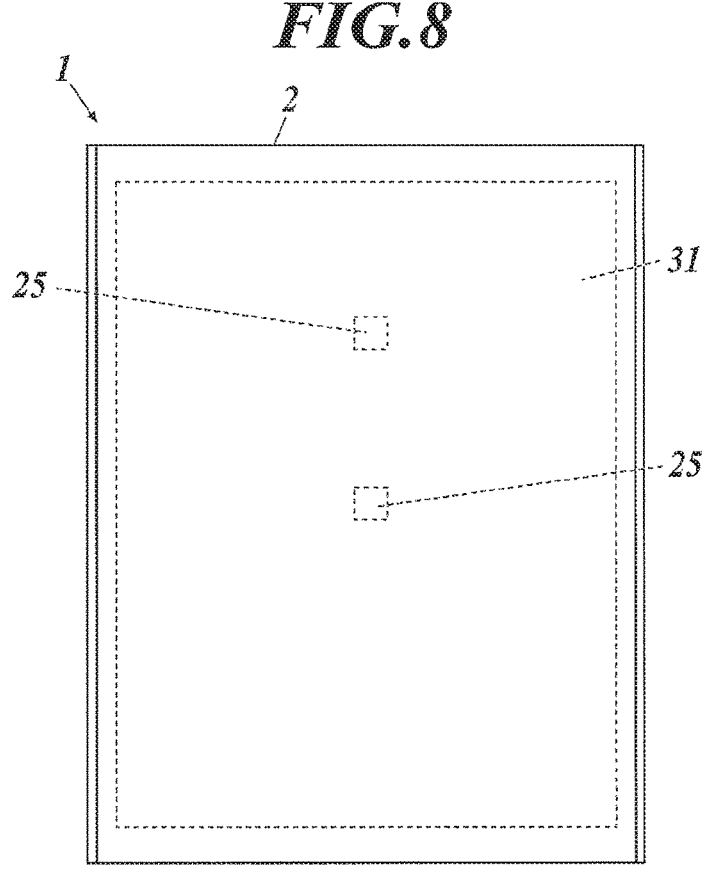

X-RAY IMAGE CAPTURING APPARATUS

CROSS-REFERENCE TO RELATED APPLICATIONS

The present U.S. patent application claims a priority under the Paris Convention of Japanese Patent Application No. 2016-097542 filed on May 16, 2016, the entirety of which is incorporated herein by references.

BACKGROUND OF THE INVENTION

Field of the Invention

The present invention relates to an X-ray image capturing apparatus that can detect the start of X-ray irradiation.

Description of Related Art

Various X-ray image capturing apparatuses have been developed which are categorized into a direct conversion type that directly converts emitted X-rays into electrical signals by generating electric charges in proportion to the dose of X-rays at detecting elements and an indirect conversion type that converts emitted X-rays into electromagnetic waves having other wavelength (e.g., visible light) with a scintillator and then converts the converted and emitted electromagnetic waves into electrical signals (i.e., image data) by generating electric charges in proportion to the energy of the electromagnetic waves at photoelectric converters (e.g., photodiodes). The detecting elements of the X-ray image capturing apparatuses of the direct conversion type and the photoelectric converters of the X-ray image capturing apparatuses of the indirect conversion type are collectively referred to as "X-ray detecting elements" throughout the specification.

These X-ray image capturing apparatuses are known as flat panel detectors (FPDs). In contrast to traditional X-ray image capturing apparatuses of a dedicated (fixed) type integrated with a support table, X-ray image capturing apparatuses of a portable (cassette) type have recently been developed for practical application, where each apparatus includes a housing accommodating X-ray detecting elements.

With reference to FIGS. 2 and 3 (described below), for example, a typical portable X-ray image capturing apparatus includes multiple X-ray detecting elements 7 disposed in a two-dimensional array or matrix and connected to respective thin-film transistors 8 (hereinafter referred to as "TFTs 8") functioning as switching elements. Typical X-ray image capturing is conducted by emitting X-rays to the X-ray image capturing apparatus from an X-ray generating apparatus with a target portion to be imaged (e.g., the front breast) of a patient (subject) theirbetween.

By performing X-ray irradiation while an OFF voltage is applied from a gate driver 15B of a scan driving unit 15 of the X-ray image capturing apparatus to scanning lines 5(L1) to 5(Lx), to turn off all the TFTs 8 (i.e., to cause the shift to a charge accumulating mode described below), the electric charges generated in the X-ray detecting elements 7 in response to the X-ray irradiation are certainly accumulated in the X-ray detecting elements 7 during the image capturing.

A typical traditional X-ray image capturing apparatus of the dedicated type cooperates with an X-ray generating apparatus while they are transmitting signals to each other, for example. In detail, the X-ray generating apparatus confirms the completion of application of OFF voltages to the scanning lines 5(L1) to 5(Lx) and the shift to the charge accumulating mode at the X-ray image capturing apparatus, and then emits X-rays.

Unfortunately, the transmission of signals between the X-ray image capturing apparatus and the X-ray generating apparatus is sometimes unavailable, for example, if they are produced by different manufacturers. No cooperation between the X-ray image capturing apparatus and the X-ray generating apparatus requires the X-ray image capturing apparatus to autonomously detect X-ray irradiation. In order to meet this requirement, various X-ray image capturing apparatuses have recently been developed capable of autonomously detecting X-ray irradiation.

For example, Japanese Patent Application Laid-Open Publication No. 2015-62012 discloses an X-ray image capturing apparatus including a control circuit that causes the shift to the charge accumulating mode when the start of X-ray irradiation is detected by one or both of a first detection scheme based on data read from X-ray detecting elements and a second detection scheme based on the value output from an X-ray sensor.

Japanese Patent Application Laid-Open Publication No. 2014-49982 discloses an X-ray image capturing apparatus including two adjacent detecting units, where a first detecting unit has lower detecting capability than a second detecting unit so that the second detecting unit can detect the end of X-ray irradiation even after saturation of the first detecting unit. The X-ray image capturing apparatus can thus certainly detect the start and end of X-ray irradiation.

In the image capturing of a highly active subject, such as an infant, X-rays are emitted at a relatively high dose rate (i.e., dose per unit time) during a short period. In the image capturing with the X-ray generating apparatus brought in a hospital ward or a house of a patient, X-rays are emitted at a relatively low dose rate during a long period because of the low output of the X-ray generating apparatus.

In these cases, the X-ray image capturing apparatus disclosed in Japanese Patent Application Laid-Open Publication No. 2015-62012 sometimes fails to accurately detect the start of X-ray irradiation. In contrast, in the X-ray image capturing apparatus disclosed in Japanese Patent Application Laid-Open Publication No. 2014-49982, the start of X-ray irradiation at a high dose rate can be detected with either of the detecting units as described above, whereas the start of the X-ray irradiation at a low dose rate can be detected with the second detecting unit having higher detecting capability. The X-ray image capturing apparatus can thus accurately detect the start of X-ray irradiation.

In the X-ray image capturing apparatus disclosed in Japanese Patent Application Laid-Open Publication No. 2014-49982, the two adjacent detecting units detect the start of X-ray irradiation. Unfortunately, if these detecting units are disposed out of a narrowed X-ray irradiation field and not irradiated with X-rays, for example, the units cannot detect the start of X-ray irradiation.

In addition, in the X-ray image capturing of a patient after any radioisotope (RI) test, for example, either of these X-ray image capturing apparatuses may unintentionally detect γ-rays emitted from the RI remaining in the body of the patient despite of no X-ray irradiation from the X-ray generating apparatus, leading to misdetection of the start of X-ray irradiation.

SUMMARY OF THE INVENTION

An object of the invention, which has been accomplished to solve the above problems, is to provide an X-ray image capturing apparatus that can accurately detect the start of X-ray irradiation without misdetection regardless of the dose rate of X-rays and in image capturing of an RI-tested patient.

To achieve the above object, an X-ray image capturing apparatus in which one aspect of the present invention is reflected includes: a plurality of scanning lines; a plurality of signal lines; at least one X-ray sensor; a plurality of X-ray detecting elements disposed in a two-dimensional array; a switching element to cause one or more electric charges to be accumulated in each of the X-ray detecting elements in response to an OFF voltage applied through each of the scanning lines, and cause the electric charges accumulated in each of the X-ray detecting elements to be released to each of the signal lines in response to an ON voltage; a scan driving unit to switch a voltage to be applied to each of the scanning lines between the ON voltage and the OFF voltage; a readout circuit to read, as image data, the electric charges released from the X-ray detecting elements; and a control circuit to detect a start of X-ray irradiation, wherein the control circuit is configured to detect the start of the X-ray irradiation by a first detection scheme based on an increase of an amount of current flowing in the X-ray image capturing apparatus due to the X-ray irradiation or a second detection scheme based on an output from the X-ray sensor, and to cause the switching element to be turned off to cause a shift to a mode where the electric charges are accumulated in the X-ray detecting elements if the start of the X-ray irradiation is detected by the first detection scheme or the second detection scheme, and in the second detection scheme, at least one detection threshold is set such that the second detection scheme has a slower response than the first detection scheme and is capable of detecting an X-ray at a lower dose rate than a dose rate detectable by the first detection scheme.

BRIEF DESCRIPTION OF THE DRAWINGS

The present invention will become more fully understood from the detailed description given hereinbelow and the appended drawings, and thus are not intended as a definition of the limits of the present invention, and wherein:

FIG. 7A is a diagram for illustrating a mask time, etc.;

FIG. 7B is a diagram for illustrating a procedure of counting the number of output pulse signals P in the case of setting the mask time;

FIG. 8 illustrates the example X-ray image capturing apparatus including multiple X-ray sensors;

PREFERRED EMBODIMENT OF THE PRESENT INVENTION

Embodiments of an X-ray image capturing apparatus will now be described with reference to the accompanying drawings.

Although the following description will focus on an X-ray image capturing apparatus of an indirect conversion type that converts emitted X-rays into electromagnetic waves having other wavelength (e.g., visible light) with a scintillator and then converts the electromagnetic waves into electrical signals, the invention may also be applied to an X-ray image capturing apparatus of a direct conversion type that directly detects X-rays at detecting elements without a scintillator.

[Configuration of X-Ray Image Capturing Apparatus]

Figure 1:
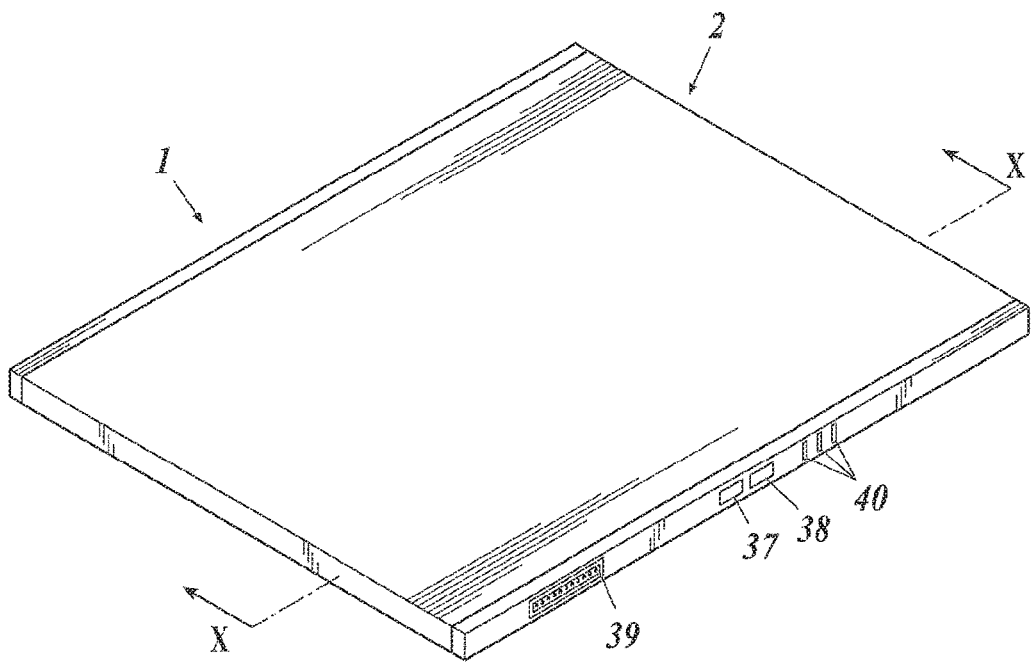
FIG. 1 is a perspective view of an X-ray image capturing apparatus according to an embodiment.
Figure 2:
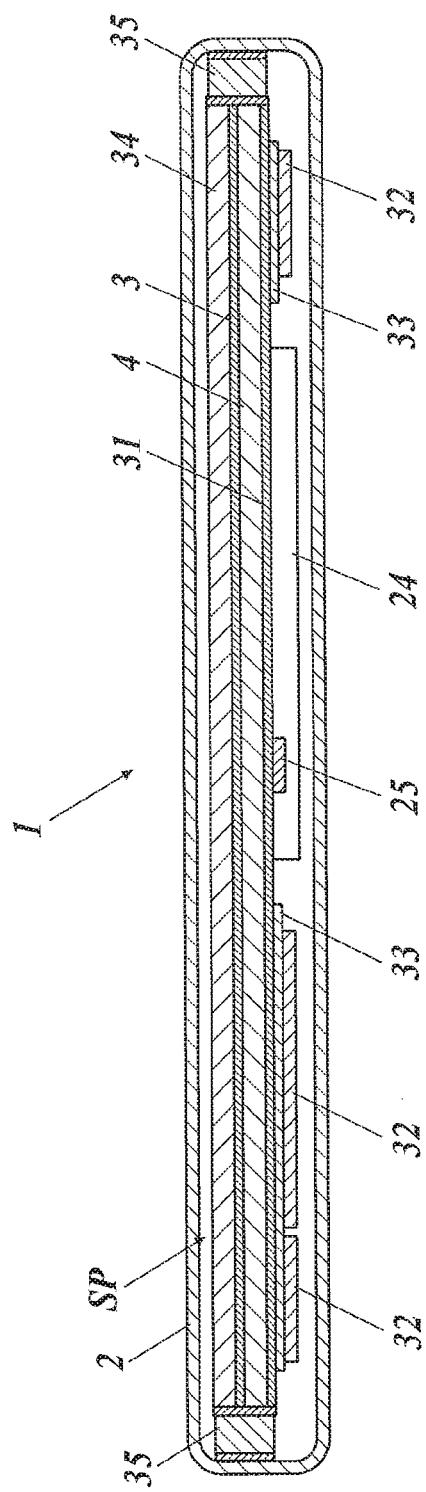
FIG. 2 is a cross-sectional view of the X-ray image capturing apparatus taken along the line X-X of FIG. 1.

FIG. 1 is a perspective view of the X-ray image capturing apparatus 1 according to the embodiment. FIG. 2 is a cross-sectional view of the X-ray image capturing apparatus 1 taken along the line X-X of FIG. 1. The vertical direction of the X-ray image capturing apparatus 1 mentioned in the following description is explained based on the arrangement state of the X-ray image capturing apparatus 1 shown in FIG. 2.

With reference to FIG. 1, one side surface of a housing 2 of the X-ray image capturing apparatus 1 is provided with a power switch 37, a toggle switch 38, a connector 39, and indicators 40. The opposite side surface of the housing 2 is provided with an antenna 41 (not shown in FIG. 1; refer to FIG. 4 described below) for wireless communication with external devices/apparatuses.

With reference to FIG. 2, the housing 2 accommodates a base plate 31. The upper surface of the base plate 31 is overlaid by a substrate 4 with a thin lead plate (not shown) therebetween. The substrate 4 is provided with X-ray detecting elements 7 on its upper surface 4A (described in detail below). The substrate 4 is disposed below a scintillator board 34 and a scintillator 3 disposed on the scintillator board 34 such that the scintillator 3 faces the X-ray detecting elements 7 of the substrate 4.

The lower surface of the base plate 31 is provided with a printed circuit board (PCB) 33 on which electronic components 32 are mounted and a built-in power source 24. The lower surface of the base plate 31 is also provided with an X-ray sensor 25. The above-described structure is a feature of a sensor panel SP in the embodiment. The sensor panel SP and each of the inner side surfaces of the housing 2 are separated with a shock-absorbing material 35 therebetween in the embodiment.

Figure 3:
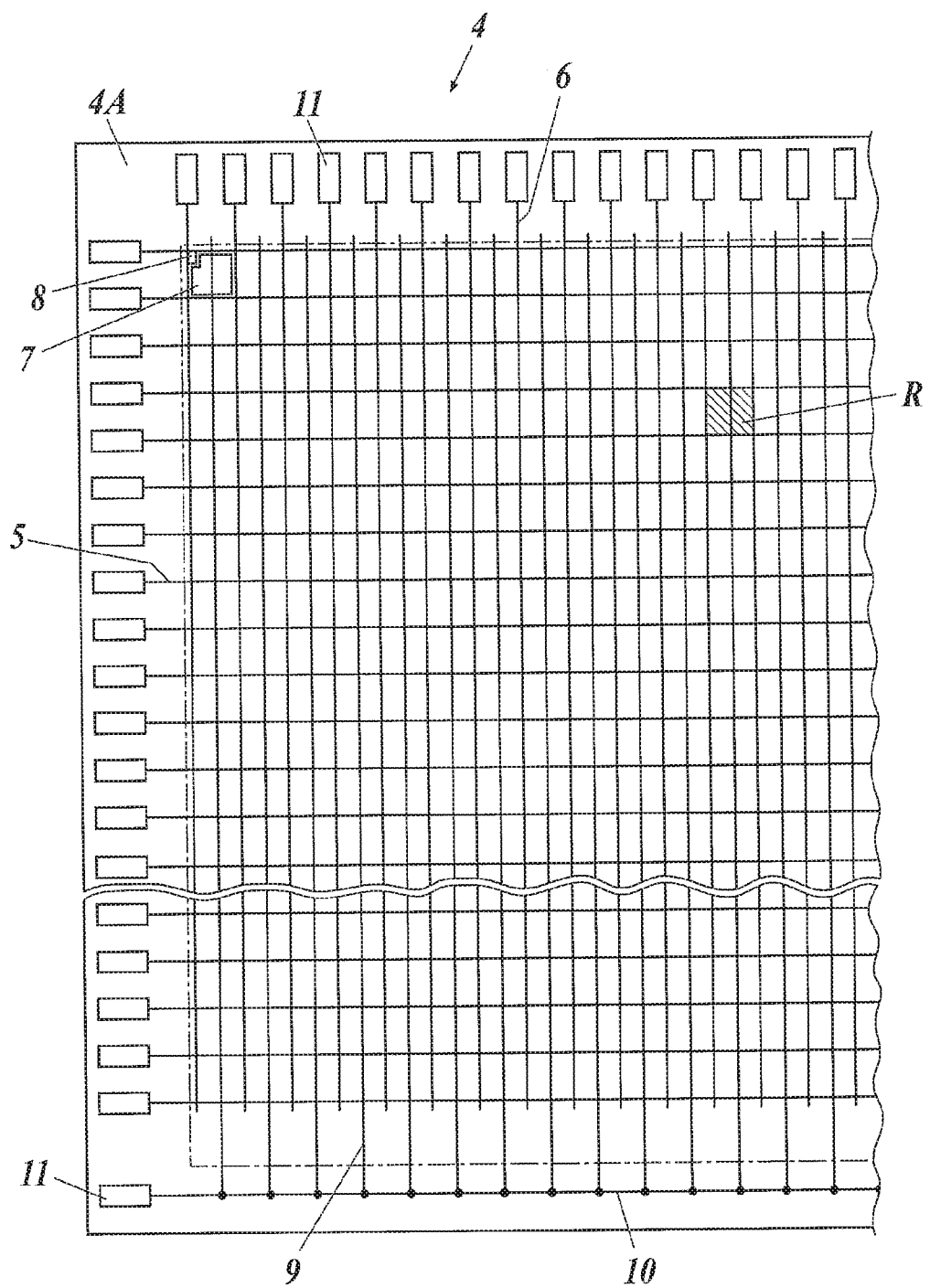
FIG. 3 is a plan view of the configuration of a substrate.

With reference to FIG. 3, the upper surface 4A, facing the scintillator 3, of the substrate 4 is equipped with multiple scanning lines 5 and intersecting multiple signal lines 6. The scanning lines 5 and the signal lines 6 define multiple areas R, each of which is provided with an X-ray detecting element 7. The X-ray detecting elements 7 are accordingly disposed in a two-dimensional array or matrix in the embodiment.

The upper surface 4A is further equipped with multiple bias lines 9 disposed in parallel to the signal lines 6 in the embodiment. The bias lines 9 are coupled to a connecting line 10. The substrate 4 is also provided with multiple input/output terminals 11 along its periphery. The input/output terminals 11 are each coupled to the scanning lines 5, the signal lines 6, and the connecting line 10. The input/output terminals 11 are connected to a flexible circuit board (not shown) composed of a film provided with chips, such as a readout IC 16 (described below), thereon. The flexible circuit board is bent so as to extend onto a back surface of the substrate 4 and is coupled to the afore-mentioned PCB 33.

Figure 4:
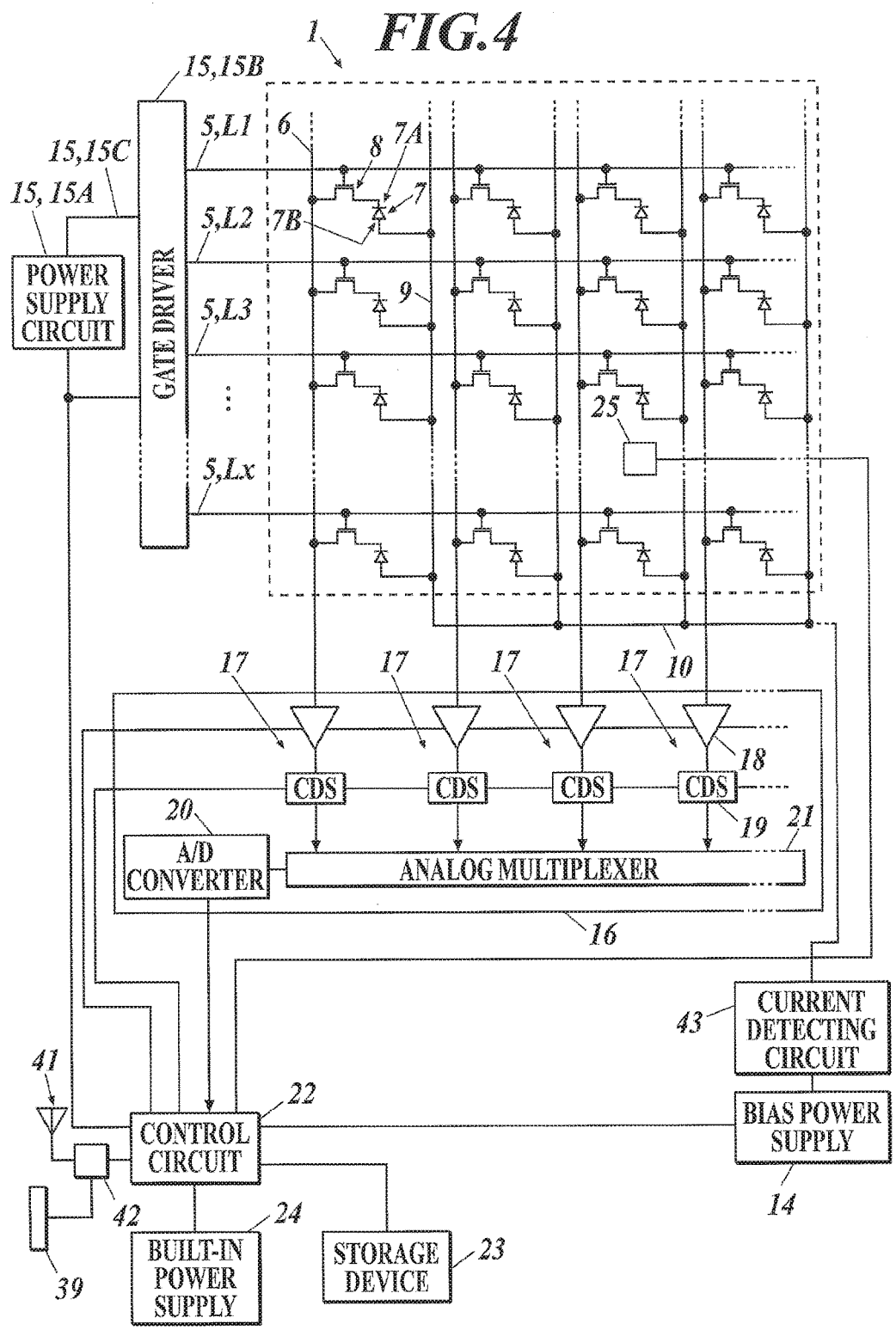
FIG. 4 is a block diagram illustrating an equivalent circuit of the X-ray image capturing apparatus.

The circuit configuration of the X-ray image capturing apparatus 1 will now be described. FIG. 4 is a block diagram illustrating an equivalent circuit of the X-ray image capturing apparatus 1 according to the embodiment. Each X-ray detecting element 7 generates electric charges in proportion to the dose of X-rays received through a subject (not shown) or in proportion to the light quantity of the electromagnetic wave having been converted at the scintillator 3. Although the X-ray detecting elements 7 are photodiodes in the following description, the X-ray detecting elements 7 may also be phototransistors or charge coupled devices (CCDs), for example.

The X-ray detecting elements 7 each have a first electrode 7A and a second electrode 7B. The second electrode 7B is connected to the corresponding bias line 9, and an inverse bias voltage is applied from a bias power supply 14 through the connecting line 10 and the bias line 9 to the X-ray detecting element 7. The first electrode 7A of the X-ray detecting element 7 is connected to the corresponding TFT 8 (functioning as a switching element). The TFT 8 is connected to the corresponding signal line 6.

ON voltages applied from a scan driving unit 15 (described below) through the scanning lines 5 turn on the TFTs 8, to release the electric charges accumulated in the X-ray detecting elements 7 to the signal lines 6. OFF voltages applied through the scanning lines 5 turn off the TFTs 8, to halt the release of electric charges from the X-ray detecting elements 7 to the signal lines 6 and allow electric charges to be accumulated in the X-ray detecting elements 7.

The scanning lines 5 are connected to a gate driver 15B of the scan driving unit 15. In the scan driving unit 15, ON and OFF voltages are supplied from a power supply circuit 15A through a line 15C to the gate driver 15B. The gate driver 15B switches voltages to be applied to the scanning lines 5(L1) to 5(Lx) between ON voltages and OFF voltages.

The signal lines 6 are also connected to respective readout circuits 17 built in the readout IC 16. In the embodiment, the readout circuits 17 each include an integrating circuit 18 and a correlated double sampling circuit 19. The readout IC 16 also includes an analog multiplexer 21 and an A/D converter 20. In FIG. 4, the correlated double sampling circuits 19 are indicated as "CDSs."

In image capturing, when the X-ray generating apparatus (not shown) irradiates the X-ray image capturing apparatus 1 with X-rays during the off-state of the TFTs 8 (functioning as switching elements), the X-ray irradiation causes electric charges to be generated and accumulated in the X-ray detecting elements 7. In a readout process for reading image data d from the X-ray detecting elements 7, the gate driver 15B of the scan driving unit 15 sequentially applies ON voltages to the scanning lines 5(L1) to 5(Lx) to release the electric charges from the respective X-ray detecting elements 7 to the corresponding signal lines 6.

These electric charges flow in the integrating circuits 18 of the readout circuits 17 and are accumulated therein, and the integrating circuits 18 then output voltage values in proportion to the accumulated electric charges. The correlated double sampling circuits 19 each output analog image data d determined by calculating the difference of the voltage values output from the corresponding integrating circuit 18 between before and after the flow of electric charges from the X-ray detecting elements 7 into the integrating circuits 18.

The analog image data d is sequentially transferred via the analog multiplexer 21 to the A/D converter 20, sequentially converted into digital image data d at the A/D converter 20, and then sequentially output to and stored in a storage device 23. The readout process for the image data d is thereby completed.

The control circuit 22 includes a computer provided with a not-shown central processing unit (CPU), a read only memory (ROM), a random access memory (RAM), and an input/output interface, which are connected to each other with buses; or a field programmable gate array (FPGA). The control circuit 22 may also be a dedicated circuit.

The control circuit 22 is connected to the storage device 23 including a static RAM (SRAM), a synchronous DRAM (SDRAM), or a NAND-type flash memory; the built-in power source 24 including a lithium ion capacitor; and the X-ray sensor 25. The control circuit 22 is also connected to a communication device 42 for wired or wireless communication with external devices/apparatuses with the connector 39 or the antenna 41.

For example, the control circuit 22 may be connected to the X-ray sensor 25 with a line shielded from noise. Alternatively, the thin lead plate on the base plate 31 (refer to FIG. 2) may have an opening in the position corresponding to the X-ray sensor 25 to allow X-rays to readily reach the X-ray sensor 25.

The control circuit 22 detects the start of X-ray irradiation by first and second detection schemes (described below). In response to detection of the start of X-ray irradiation by one or both of the first and second detection schemes, OFF voltages are applied from the gate driver 15B of the scan driving unit 15 to the scanning lines 5(L1) to 5(Lx) to turn off the TFTs 8. This process causes the shift to the charge accumulating mode where the X-ray detecting elements 7 accumulate electric charges generated in response to X-ray irradiation.

After elapse of a predetermined time from the shift to the charge accumulating mode, the control circuit 22 controls the gate driver 15B to sequentially apply ON voltages to the scanning lines 5(L1) to 5(Lx), and controls the readout circuits 17 to execute the readout operation for reading the image data d from the X-ray detecting elements 7, as described above.

[Detection Schemes for Detecting Start of X-Ray Irradiation]

In the embodiment, the control circuit 22 uses two detection schemes for detecting the start of X-ray irradiation.

[First Detection Scheme]

In the first detection scheme, the control circuit 22 detects the start of X-ray irradiation based on an increase of current flowing in the X-ray image capturing apparatus 1 due to X-ray irradiation. With reference to FIG. 4, the connecting line 10 connecting the bias lines 9 is provided with a current detecting circuit 43 for detecting a current I flowing in the connecting line 10 in the embodiment. The start of X-ray irradiation is detected based on the current I (in the embodiment, the below-described integrated value ΣI of the current I) detected at the current detecting circuit 43.

Figure 5A:
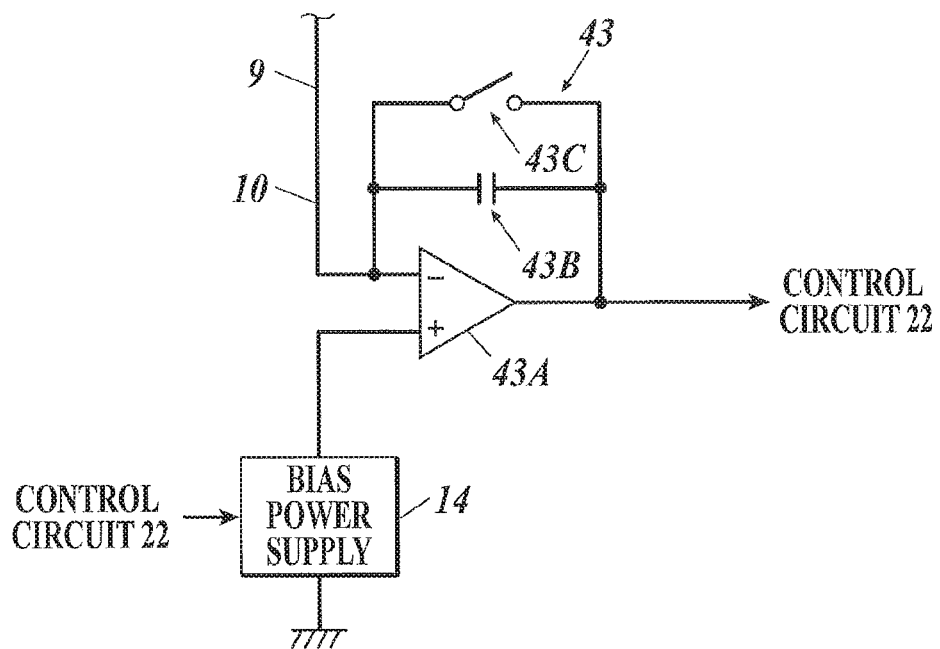
FIG. 5A illustrates an example configuration of a current detecting circuit.

With reference to FIG. 5A, for example, the current detecting circuit 43 may be an integrating circuit. In detail, the current detecting circuit 43 includes an operational amplifier 43A, a capacitor 43B, and a switch 43C, for example. The inverting input terminal and the output terminal of the operational amplifier 43A is connected to each other via the capacitor 43B and the switch 43C.

The non-inverting input terminal of the operational amplifier 43A is connected to the bias power supply 14, whereas the inverting input terminal of the operational amplifier 43A is connected to the connecting line 10 leading to the bias lines 9. In the embodiment, an inverse bias voltage is applied from the bias power supply 14 via the operational amplifier 43A of the current detecting circuit 43 to the connecting line 10 and the bias lines 9.

In the embodiment, the current I flowing in the bias lines 9 and the connecting line 10 enters the capacitor 43B of the current detecting circuit 43, so that electric charges are accumulated in the capacitor 43B. The current detecting circuit 43 then outputs a voltage value (corresponding to the integrated value ΣI of the current I) in proportion to the potential difference between the electrodes of the capacitor 43B. The voltage output from the current detecting circuit 43 has a negative value in the embodiment. The voltage is thus inverted into a positive value, converted into a digital value, and/or subjected to other processing, and then output to the control circuit 22.

Although the current detecting circuit 43 actually outputs a voltage value, the following description is simplified by assuming that the current detecting circuit 43 outputs the integrated value ΣI of the detected current I. The target detected at the current detecting circuit 43 is not necessarily the integrated value ΣI of the current I as in the embodiment but also the current I itself flowing in the bias lines 9 and the connecting line 10.

Figure 5B:
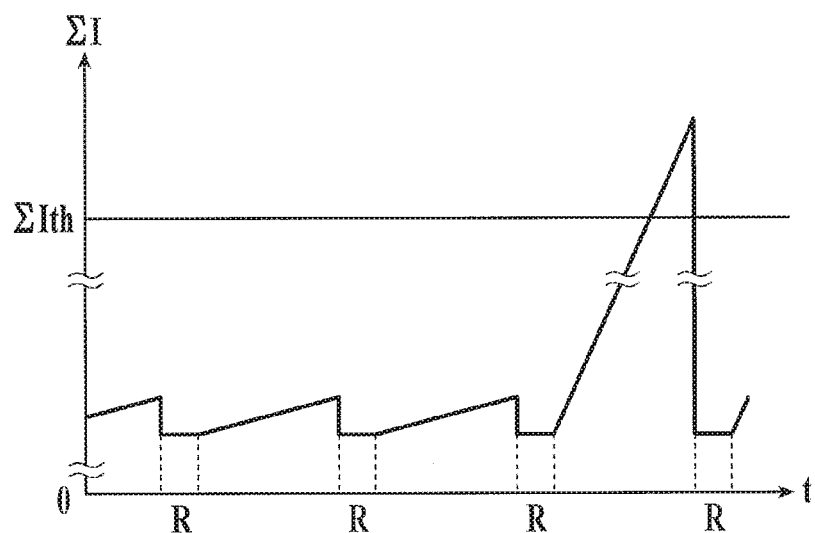
FIG. 5B illustrates a temporal variation in integrated value of current output from the current detecting circuit.

With reference to FIG. 5B, the switch 43C is turned on to execute resetting processes (refer to R in FIG. 5B) in predetermined time intervals in the embodiment. This processes can prevent the capacitor 43B from being saturated by continuous inflow of the current I into the capacitor 43B. Even during no X-ray irradiation of the X-ray image capturing apparatus 1, the X-ray detecting elements 7 generate dark charges (also called dark currents) to cause a small current I to flow in the connecting line 10 connected to the bias lines 9. The integrated value ΣI of the current I output from the current detecting circuit 43 thus repeats the state of gradually increasing and then being reset, as illustrated in FIG. 5B.

In response to X-ray irradiation of the X-ray image capturing apparatus 1, the X-ray detecting elements 7 generate electric charges several orders of magnitude higher than the dark charges, to thereby vary the electric potential between the electrodes 7A and 7B of each X-ray detecting element 7. To compensate for this potential variation, the current I flowing in the bias lines 9 and the connecting line 10 significantly increases, as illustrated in FIG. 5B.

In the embodiment, a detection threshold ΣIth is predetermined for the integrated value ΣI of the current I detected at the current detecting circuit 43. If the integrated value ΣI of the current I detected at the current detecting circuit 43 exceeds the detection threshold ΣIth, the control circuit 22 detects the start of X-ray irradiation. This detection scheme is explained in detail in, for example, Japanese Patent Application Laid-Open Publication No. 2009-219538.

Although the following description assumes the above-described configuration, the above configuration should not be construed to limit the first detection scheme. In detail, the start of X-ray irradiation may be detected based on, for example, an increase of current flowing in the scanning lines 5 or the signal lines 6 in response to the start of X-ray irradiation, instead of an increase of current flowing in the bias lines 9 and the connecting line 10 used in the embodiment. That is, the first detection scheme only has to use any increase of an amount of current flowing in the X-ray image capturing apparatus 1 due to X-ray irradiation to detect the start of X-ray irradiation, and the illustrated embodiment should not be construed to limit the invention.

In the embodiment, the X-ray detecting elements 7 generate dark charges even during no X-ray irradiation of the X-ray image capturing apparatus 1 as described above; hence, an offset o due to these dark charges is superposed on the current I detected at the current detecting circuit 43. In order to determine the offset o, the integrated value ΣI of the current I flowing in the connecting line 10 during no X-ray irradiation of the X-ray image capturing apparatus 1 is detected at the current detecting circuit 43, and stored as an integrated value Σo of the offset o generated by the dark charges, for example.

In practice, a temporal variation in the integrated value ΣI of the current I from the reset to the subsequent reset (refer to FIG. 5B) is stored as a temporal variation in the integrated value Σo of the offset o. Alternatively, the stored temporal variation in the integrated value Σo of the offset o may be the average of determined multiple temporal variations. The detection scheme for detecting the start of X-ray irradiation can use the value calculated by subtracting the integrated value Σo of the offset o from the integrated value ΣI of the current I detected at the current detecting circuit 43.

The integrated value ΣI of the current I detected at the current detecting circuit 43 or the current I itself is then subject to a low-pass filtering process to remove high-frequency noise. This process can prevent the X-ray image capturing apparatus 1 from misdetecting the start of X-ray irradiation due to the electromagnetic waves emitted from a device near the X-ray image capturing apparatus 1 and due to shocks or vibrations applied to the X-ray image capturing apparatus 1, for example. In such a case, the time constant of the low-pass filter is appropriately adjusted.

[Second Detection Scheme]

Figure 6:
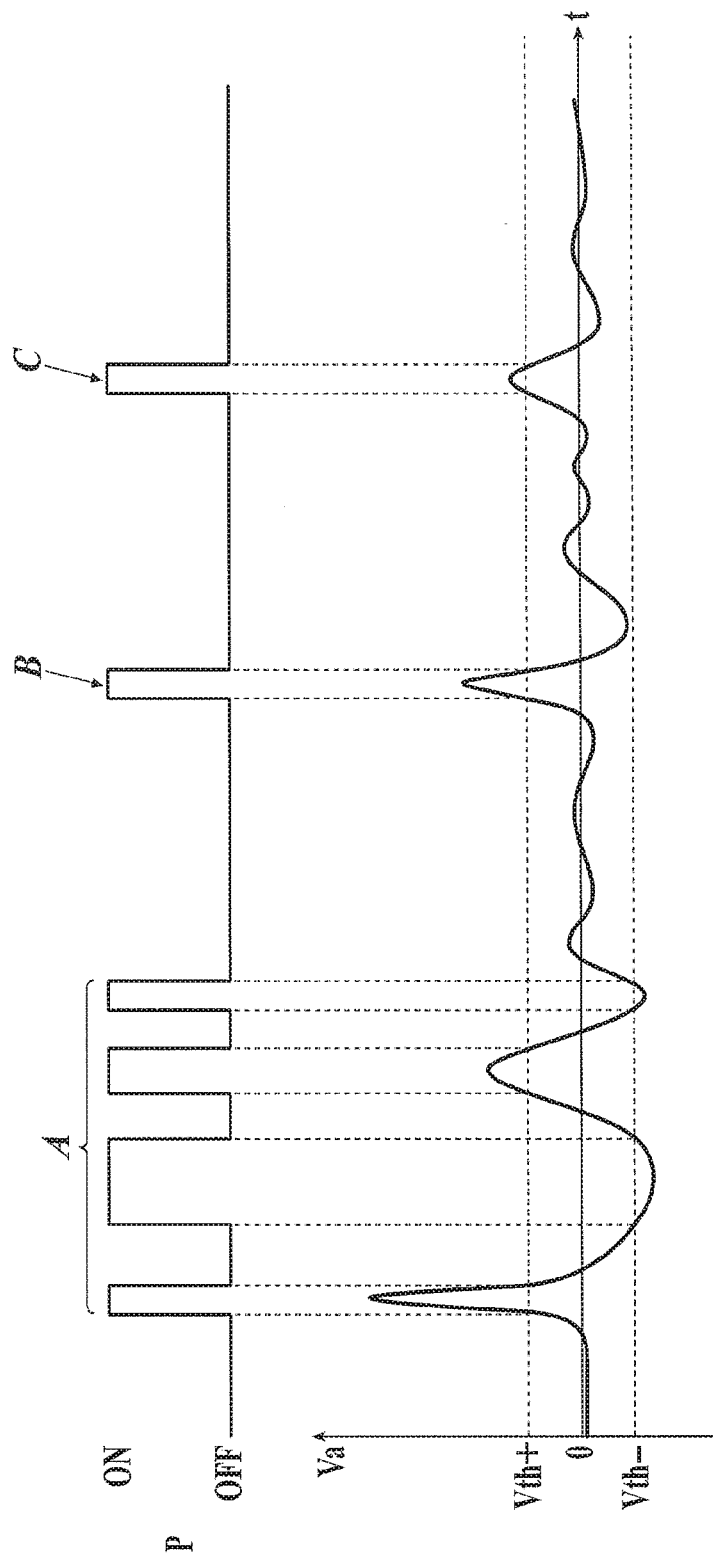
FIG. 6 illustrates a temporal variation in analog voltage value of an X-ray sensor (in the lower chart) and example pulse signals output in response to the voltage value (in the upper chart)

In the second detection scheme, the control circuit 22 detects the start of X-ray irradiation based on the output from the X-ray sensor 25. The X-ray sensor 25 is a photon counting sensor in the embodiment. With reference to FIG. 6, the analog voltage value Va of the X-ray sensor 25 varies in response to X-ray irradiation in the embodiment. The X-ray sensor 25 outputs a pulse signal P when the voltage value Va exceeds a positive set value Vth+ or falls below a negative set value Vth−.

When X-ray is applied from the X-ray generating apparatus to the X-ray sensor 25, a single X-ray photon incident on the X-ray sensor 25 causes the X-ray sensor 25 to output a single pulse signal P, as indicated by a pulse B or C in FIG. 6, for example. In high-energy radiation (e.g., high-energy natural radiation) emission to the X-ray sensor 25, where the voltage value Va largely varies, only a single photon incident on the X-ray sensor 25 causes generation of multiple pulse signals P, as indicated by pulses A in FIG. 6, for example.

That is, the multiple pulse signals P output from the X-ray sensor 25 alone cannot discriminate the pulse signals P in response to X-ray irradiation at a high dose rate from the X-ray generating apparatus from the pulse signals P in response to high-energy natural radiation emission. In other words, the multiple pulse signals P generated in response to incident high-energy natural radiation emission may be mistaken for those generated in response to X-ray irradiation from the X-ray generating apparatus.

In order to avoid such misdetection, when the pulse signal P is output from the X-ray sensor 25, the control circuit 22 does not perform at least determination of whether or not pulse signals P are output from the X-ray sensor 25 for a predetermined mask time Δtm since the pulse signal P is output from the X-ray sensor 25 in the embodiment.

In detail, with reference to FIG. 7A, the control circuit 22 ignores pulse signals P output from the X-ray sensor 25 until the predetermined mask time Δtm elapses since the pulse signal P is output from the X-ray sensor 25. The control circuit 22 thus determines that a single pulse signal P is output from the X-ray sensor 25 within the mask time Δtm after the X-ray sensor 25 outputs the first pulse signal P, regardless of the number of the pulse signals P that are actually output.

With reference to FIG. 7B, for example, the third pulse signal P subsequent to the second pulse signal P is output from the X-ray sensor 25 within the mask time Δtm, and thus is not counted by the control circuit 22.

The control circuit 22 of the embodiment is configured to determine that X-ray irradiation has been started at the time when a predetermined number N of pulse signals P are output within a predetermined time ΔT since the pulse signal P is output from the X-ray sensor 25 as described above, under the restriction condition using the mask time Δtm as illustrated in FIG. 7B, for example.

Specifically, with reference to FIG. 7B, if three pulse signals P are output within the predetermined time ΔT in the case of the predetermined number N being 3, the control circuit 22 determines the start of X-ray irradiation in response to output of the third pulse signal P.

Additionally, even when the X-ray sensor 25 outputs multiple pulse signals P within a short period in response to shocks or vibrations applied to the X-ray image capturing apparatus 1, the control circuit 22 determines the number of output pulse signals P to be one as illustrated in FIG. 7A. After disappearance of the shocks or vibrations from the X-ray image capturing apparatus 1, the X-ray sensor 25 does not output any pulse signal P.

Since the predetermined number N of pulse signals P are not output within the predetermined time ΔT after the output of the first pulse signal P even when shocks or vibrations are applied to the X-ray image capturing apparatus 1, the control circuit 22 does not determine that X-ray irradiation has been started. The second detection scheme in the embodiment can thus avoid misdetection of the start of X-ray irradiation regardless of shocks or vibrations applied to the X-ray image capturing apparatus 1.

The X-ray image capturing apparatus 1 is equipped with a single X-ray sensor 25 in FIG. 2 or 4, but may also include multiple X-ray sensors 25 as illustrated in FIG. 8, for example. The X-ray sensors 25 may be disposed not only in the center of the lower surface of the base plate 31 but also positions other than the center. The number of X-ray sensors 25 is two in FIG. 8, but may also be three or more.

X-ray irradiation of the X-ray image capturing apparatus 1 can thus be detected with any of the X-ray sensors 25 despite of a narrowed area of X-ray irradiation, leading to more accurate detection of the start of X-ray irradiation by the second detection scheme. In the embodiment, if the narrowed area of X-ray irradiation is deviated from the position(s) of the X-ray sensor(s) 25, the start of X-ray irradiation can be detected by the first detection scheme.

[Features of Detection Schemes in the Embodiment]

With reference to FIG. 5B, in the first detection scheme in the embodiment, if the X-ray image capturing apparatus 1 is irradiated with intense X-rays (i.e., X-rays at a high dose rate), the integrated value ΣI of the current I detected at the current detecting circuit 43 increases at a significantly high rate and immediately exceeds the detection threshold ΣIth. The start of X-ray irradiation at a high dose rate can thus be immediately detected (i.e., with high response).

Figure 9:
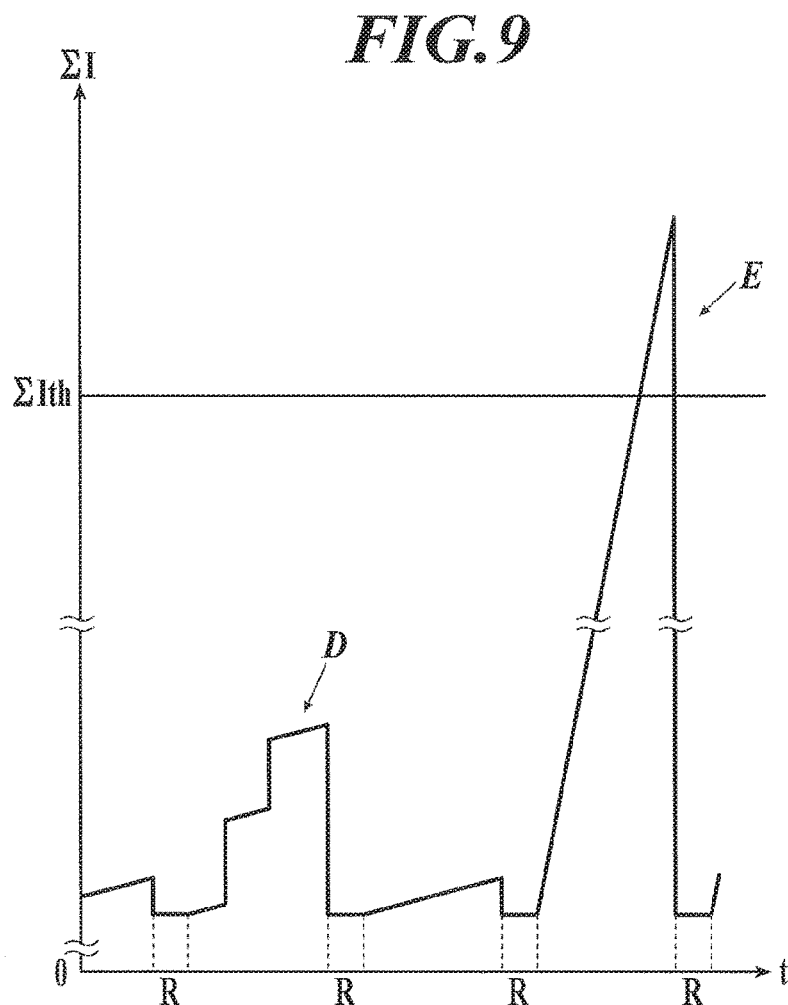
FIG. 9 illustrates a temporal variation in integrated value of current output from the current detecting circuit through the experience of a shock to the X-ray image capturing apparatus and X-ray irradiation.

As indicated by D in FIG. 9, if shocks or vibrations are applied to the X-ray image capturing apparatus 1, for example, the integrated value ΣI of the current I detected at the current detecting circuit 43 temporarily increases but does not exceed the detection threshold ΣIth. The shocks or vibrations applied to the X-ray image capturing apparatus 1 are thus not mistaken for the start of X-ray irradiation in the embodiment. In contrast, as indicated by E in FIG. 9, if the X-ray image capturing apparatus 1 is irradiated with X-rays, the integrated value ΣI of the current I detected at the current detecting circuit 43 rapidly increases and exceeds the detection threshold ΣIth. This configuration in the embodiment can accurately detect the start of X-ray irradiation of the X-ray image capturing apparatus 1.

Conversely, the detection threshold ΣIth has a relatively high value to prevent the shocks or vibrations from being mistaken for the start of X-ray irradiation in the embodiment. The start of X-ray irradiation of the X-ray image capturing apparatus 1 can thus be accurately detected without misdetection caused by shocks or vibrations applied to the X-ray image capturing apparatus 1 according to the embodiment.

A narrow dynamic range of the integrated value ΣI of the current I (i.e., in the y-axis direction in FIG. 9) detected at the current detecting circuit 43, in other words, a narrow dynamic range of dose rate of detectable X-rays more readily saturates the integrated value ΣI of the current I. This feature hinders appropriate adjustment of the detection threshold ΣIth for discriminating the increases in the integrated value ΣI of the current I generated by X-ray irradiation from the increases caused by the shocks or vibrations, unlike the above-described configuration. In order to avoid this problem, the dynamic range of the integrated value ΣI of the current I detectable at the current detecting circuit 43 (i.e., the dynamic range of dose rate of detectable X-rays) is determined as large as possible in the embodiment.

In the second detection scheme in the embodiment, the start of X-ray irradiation is detected when the predetermined number N of pulse signals P are output from the X-ray sensor 25 (within the predetermined time ΔT), as described above. The second detection scheme is thus adjusted to have slower response than the first detection scheme capable of immediate detection of the start of X-ray irradiation.

At a low dose rate of X-rays from the X-ray generating apparatus, the X-ray irradiation sometimes cannot be detected by the first detection scheme, because the integrated value ΣI of the current I detected at the current detecting circuit 43 only slightly increases and does not reach the detection threshold ΣIth between the resets (refer to R in FIG. 9). In this case, the start of X-ray irradiation can certainly be detected by the second detection scheme if the X-ray sensor 25 outputs at least the predetermined number N of pulse signals P within the predetermined time ΔT, as illustrated in FIG. 7B.

In the embodiment, the control circuit 22 uses the first detection scheme for detecting the start of X-ray irradiation at a higher dose rate from the X-ray generating apparatus, and uses the second detection scheme for detecting the start of X-ray irradiation at a lower dose rate than the dose rate detectable by the first detection scheme from the X-ray generating apparatus.

In order to accurately detect the start of X-ray irradiation at a lower dose rate than the dose rate detectable by the first detection scheme, the dynamic range of dose rate of detectable X-rays in the second detection scheme is adjusted appropriately for X-rays at the lower dose rate, although the dynamic range does not have to be as large as that in the first detection scheme. The predetermined time $\Delta T$ and the predetermined number N (detection thresholds) in the second detection scheme are also appropriately determined such that X-ray at a lower dose rate than the dose rate detectable by the first detection scheme can be detected.

Figure 10A:
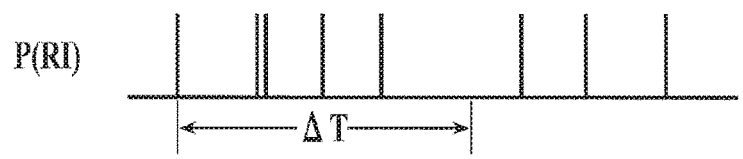
FIG. 10A illustrates example timings of outputting pulse signals from an X-ray sensor in response to γ-rays emitted from the inside of the body of a patient after an RI-test.
Figure 10B:
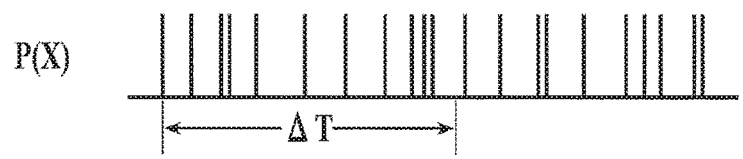
FIG. 10B illustrates example timings of outputting pulse signals from an X-ray sensor in response to X-ray irradiation from an X-ray generating apparatus.

It is needless to say that the X-rays at a dose rate detectable by the first detection scheme can also be detected by the second detection scheme. In the X-ray image capturing of a patient after any radioisotope (RI) test, the $\gamma$-rays emitted from the inside of the body of the patient at a certain frequency should not be detected by the second detection scheme to avoid misdetection of the start of X-ray irradiation. Comparing the frequency of $\gamma$-ray emission from the RI-tested patient (the frequency of pulse signals P(RI) output from the X-ray sensor 25) with the frequency of arrival of X-ray photons to the X-ray sensor 25 when the X-ray generating apparatus emits X-ray at a low dose rate (the frequency of pulse signals P(X) output from the X-ray sensor 25), the frequency in the case that the X-ray at a low dose rate is emitted (see FIG. 10B) is generally higher than the frequency of $\gamma$-ray emission from the patient (see FIG. 10A).

Accordingly, the appropriate determination of the predetermined time $\Delta T$ and the predetermined number N (detection thresholds) in the second detection scheme leads to accurate detection of the start of X-ray irradiation at a low dose rate, and can also significantly reduce the risk of misdetection of the start of X-ray irradiation despite of no X-ray irradiation due to the $\gamma$-ray emitted from the inside of the body of the RI-tested patient.

That is, the second detection scheme in the embodiment has slower response than the first detection scheme, as described above, but can accurately discriminate the X-ray irradiation at a low dose rate from the $\gamma$-ray emission from the inside of the body of the RI-tested patient using a relatively long time (the predetermined time $\Delta T$).

Figure 11:
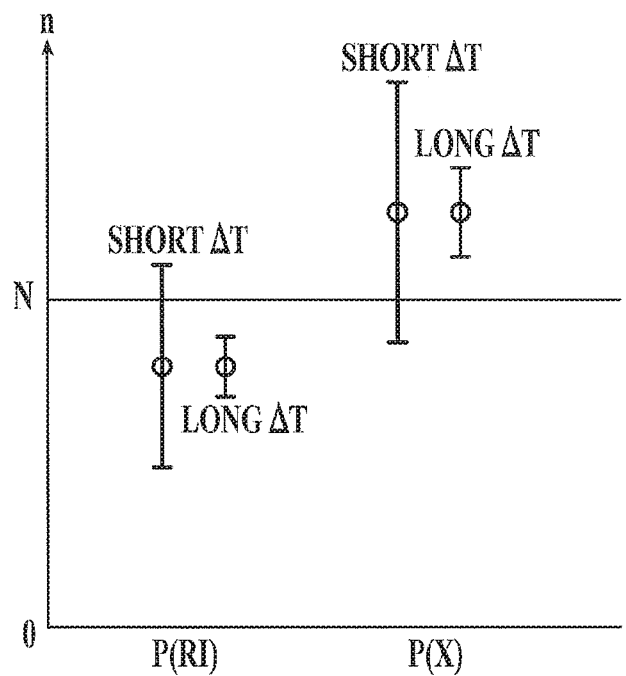
FIG. 11 is a diagram for illustrating a decrease in dispersion of the number of output pulse signals from an X-ray sensor caused by an increase in a predetermined time.

With reference to FIG. 11, the discrimination using a relatively long predetermined time $\Delta T$ provides a smaller dispersion (error) of the number n of pulse signals P(RI) and the number n of pulse signals P(X) output from the X-ray sensor 25 than the discrimination using a short predetermined time $\Delta T$. In addition, the appropriately predetermined number N can contribute to accurate discrimination of the X-ray irradiation at a low dose rate (refer to P(X)) from the $\gamma$-ray emission from the inside of the body of the RI-tested patient (refer to P(RI)).

In the embodiment, the relatively long predetermined time $\Delta T$ and the appropriately predetermined number N (detection thresholds) in the second detection scheme can achieve accurate detection of the start of X-ray irradiation at a low dose rate and effectively reduce the risk of misdetection caused by $\gamma$-ray emission from the inside of the body of the RI-tested patient.

[Operations]

Operations of the X-ray image capturing apparatus 1 will now be explained according to the embodiment.

In the X-ray image capturing apparatus 1 according to the embodiment, if the X-ray generating apparatus irradiates the X-ray image capturing apparatus 1 with X-rays at a relatively high dose rate for a short period in the image capturing of a highly active subject, such as an infant, the integrated value $\Sigma I$ of the current I flowing in the bias lines 9 and the connecting line 10 and detected at the current detecting circuit 43 rapidly increases and exceeds the detection threshold $\Sigma I th$, as illustrated in FIG. 5B. In this case, the control circuit 22 can accurately detect the start of X-ray irradiation of the X-ray image capturing apparatus 1 at a high dose rate for a short period based on the first detection scheme.

If the X-ray generating apparatus providing low output irradiates the X-ray image capturing apparatus 1 with X-rays at a relatively low dose rate for a long period, for example, the first detection scheme may be inappropriate because of the integrated value $\Sigma I$ of the current I not reaching the detection threshold $\Sigma I th$ between the resets. In contrast, with reference to FIG. 7B, the second detection scheme detects the start of X-ray irradiation when the number of output pulse signals P reaches the predetermined number N within the predetermined time $\Delta T$. The control circuit 22 can thus accurately detect the start of X-ray irradiation of the X-ray image capturing apparatus 1 at a low dose rate for a long period based on the second detection scheme.

In the case that $\gamma$-rays are emitted at a certain frequency from the inside of the body of an RI-tested patient (refer to FIG. 10A), for example, although the current I flowing in the bias lines 9 and the connecting line 10 slightly increases because of electric charges generated in the X-ray detecting elements 7 in response to the $\gamma$-rays, the integrated value $\Sigma I$ of the current I detected at the current detecting circuit 43 does not exceed the detection threshold $\Sigma I th$ between the resets in the first detection scheme.

The control circuit 22 thus does not misdetect the start of X-ray irradiation by the first detection scheme without X-ray irradiation from the X-ray generating apparatus, regardless of $\gamma$-rays emitted from the inside of the body of the patient at a certain frequency.

In addition, for example, even when $\gamma$-rays are emitted from the inside of the body of the RI-tested patient at a certain frequency, the control circuit 22 does not misdetect the start of X-ray irradiation by the second detection scheme without X-ray irradiation from the X-ray generating apparatus, provided that the predetermined time $\Delta T$ and the predetermined number N (detection thresholds) in the second detection scheme are appropriately predetermined.

In contrast, if the above-described conditions in the first or second detection scheme are satisfied after the start of X-ray irradiation from the X-ray generating apparatus, the control circuit 22 accurately detects the start of X-ray irradiation, as explained above.

That is, in image capturing of the RI-tested patient in the embodiment, the control circuit 22 does not mistake the $\gamma$-ray emission from the inside of the body of the RI-tested patient for the start of X-ray irradiation and can accurately detect the start of X-ray irradiation from the X-ray generating apparatus, thereby achieving appropriate image capturing of the patient.

In the embodiment, the control circuit 22 does not detect the start of X-ray irradiation in response to shocks or vibrations applied to the X-ray image capturing apparatus 1 by either of the first and second detection schemes, as explained above. The configuration in the embodiment can thus certainly prevent the misdetection of the start of X-ray irradiation caused by shocks or vibrations applied to the X-ray image capturing apparatus 1.

The configuration in the embodiment can also certainly prevent the misdetection of the start of X-ray irradiation caused by high-energy natural radiation emission to the X-ray sensor 25, as explained above.

[Advantageous Effects]

As explained above, in the X-ray image capturing apparatus 1 according to the embodiment, the control circuit 22 can accurately detect the start of X-ray irradiation without misdetection regardless of the dose rate of X-rays on the X-ray image capturing apparatus 1 and in image capturing of an RI-tested patient.

In detail, the start of X-ray irradiation can be accurately detected without misdetection, for example, in either case of a relatively high dose rate of X-rays for a short period in the image capturing of a highly active subject, such as an infant, and of a relatively low dose rate of X-rays for a long period because of the low output of the X-ray generating apparatus.

The start of X-ray irradiation can also be accurately detected without misdetection in X-ray image capturing of the body of the RI-tested patient emitting γ-rays.

[Modification]

In the above-described embodiment, the control circuit 22 detects the start of X-ray irradiation of the X-ray image capturing apparatus 1 at a high dose rate by the first detection scheme, and detects the start of X-ray irradiation at a low dose rate by the second detection scheme. The X-ray irradiation at an intermediate dose rate (i.e., a dose rate not high but not low) can be detected by either of the first and second detection schemes.

If the first detection scheme is used to detect the start of X-ray irradiation at a relatively low dose rate (i.e., at the intermediate dose rate), however, the detection threshold $\Sigma$Ith must be adjusted to a relatively small value. This relatively small detection threshold $\Sigma$Ith can be readily exceeded by the integrated value $\Sigma$I of the current I increased by γ-rays emitted from the inside of the body of the RI-tested patient, thereby causing the risk of misdetection of the start of X-ray irradiation.

In order to avoid this problem, the second detection scheme may use not only a single predetermined time $\Delta T$ and a single predetermined number N (detection thresholds; hereinafter referred to as "predetermined time $\Delta Ta$" and "predetermined number Na," respectively) in the above-described embodiment but also plural kinds of detection thresholds, i.e., may additionally use another predetermined time $\Delta Tb$ or predetermined number Nb. This configuration allows the second detection scheme to be applicable to the case of X-ray irradiation at a slightly high dose rate (i.e., the intermediate dose rate).

In this case, the intermediate dose rate of X-rays slightly higher than the above-mentioned low dose rate increases the number of pulse signals P output from the X-ray sensor 25 per unit time. In response to this increase, the predetermined time $\Delta Tb$ may be determined to be shorter than the predetermined time $\Delta Ta$ while maintaining the predetermined number N. Alternatively, the predetermined number Nb may be determined to be larger than the predetermined number Na while maintaining the predetermined time $\Delta T$. Alternatively, the predetermined time $\Delta Tb$ may be determined to be shorter than the predetermined time $\Delta Ta$, whereas the predetermined number Nb may be determined to be larger than the predetermined number Na.

In addition, each of the thresholds (i.e., positive set value Vth+ and negative set value Vth− described above) set in the X-ray sensor 25 may include plural kinds of thresholds so as to deal with the case of the intermediate dose rate of X-rays slightly higher than the above-mentioned low dose rate by the second detection scheme. The start of X-ray irradiation can thus be accurately detected by the second detection scheme at the intermediate dose rate.

The above-described configuration does not require a decrease in the detection threshold $\Sigma$Ith in the first detection scheme, and thus can further reduce the risk of misdetection by the first detection scheme. The configuration can also extend the range of accurate detection of the start of X-ray irradiation by the second detection scheme to encompass the intermediate dose rate. In these cases, the other parameters, such as the mask time $\Delta tm$, are appropriately adjusted.

The X-ray sensor 25 is of a pulse output type that detects X-rays and outputs pulse signals in the above-described embodiment, but may also be of a continuous output type that extracts continuous output signals by integrating electric charge signals generated by X-rays. In this case, the output signals in the continuous output type are subject to a low-pass filtering process having a lower time constant than that in the first detection scheme and are detected using a detection threshold capable of detecting a lower dose rate than that in the first detection scheme. The continuous output type can thereby provide advantageous effects equal to those of the pulse output type.

Furthermore, application of multiple combinations of low-pass filters and detection thresholds to the output signals in the continuous output type can extend the range of dose rate detectable by the second detection scheme.

The above-described embodiments should not be construed to limit the invention and may be appropriately modified within the gist of the invention.

What is claimed is:

1. An X-ray image capturing apparatus comprising:
   a plurality of scanning lines;
   a plurality of signal lines;
   at least one X-ray sensor;
   a plurality of X-ray detecting elements disposed in a two-dimensional array;
   a switching element to cause one or more electric charges to be accumulated in each of the X-ray detecting elements in response to an OFF voltage applied through each of the scanning lines, and cause the electric charges accumulated in each of the X-ray detecting elements to be released to each of the signal lines in response to an ON voltage;
   a scan driving unit to switch a voltage to be applied to each of the scanning lines between the ON voltage and the OFF voltage;
   a readout circuit to read, as image data, the electric charges released from the X-ray detecting elements; and
   a control circuit to detect a start of X-ray irradiation, wherein
   the control circuit is configured to detect the start of the X-ray irradiation by both a first detection scheme based on an increase of an amount of current flowing in the X-ray image capturing apparatus due to the X-ray irradiation and a second detection scheme based on an output from the X-ray sensor, and to cause the switching element to be turned off to cause a shift to a mode where the electric charges are accumulated in the X-ray detecting elements when the start of the X-ray irradiation is detected by the first detection scheme or the second detection scheme, and
   the second detection scheme has a slower response than the first detection scheme and has a narrower dynamic range of dose rate of detectable X-ray than the first detection scheme, and a detection threshold is set in the second detection scheme such that an X-ray is detectable at a lower dose rate than in the first detection scheme.

2. The X-ray image capturing apparatus of claim 1, wherein the control circuit detects, in the first detection scheme, the start of the X-ray irradiation based on a current flowing in the scanning lines, a current flowing in the signal lines, or a current flowing in a bias line or a connecting line through each of which an inverse bias voltage is applied to each of the X-ray detecting elements.

3. The X-ray image capturing apparatus of claim 1, wherein the X-ray sensor comprises a plurality of X-ray sensors.

4. The X-ray image capturing apparatus of claim 1, wherein the detection threshold in the second detection scheme comprises plural kinds of detection thresholds.

5. The X-ray image capturing apparatus of claim 1, wherein
the X-ray sensor is configured to output a pulse signal when a voltage value of the X-ray sensor generated by the X-ray irradiation exceeds at least one predetermined set value, and
the predetermined set value comprises plural kinds of predetermined set values.

6. The X-ray image capturing apparatus of claim 1, wherein
the X-ray sensor is a photon counting sensor, and
the control circuit determines the start of X-ray irradiation in response to output of a predetermined number of pulse signals within a predetermined time.

7. The X-ray image capturing apparatus of claim 6, wherein
the control circuit does not determine whether or not the pulse signal is output for a predetermined mask time since the pulse signal is output from the X-ray sensor.

8. The X-ray image capturing apparatus of claim 1, wherein
the X-ray sensor is of a type that extracts a continuous output signal by integrating an electric charge signal generated by the X-ray, the continuous output signal being subject to a low-pass filtering having a lower time constant in the second detection scheme than in the first detection scheme.

* * * * *